(12) United States Patent
Safavi

(10) Patent No.: US 10,155,055 B2
(45) Date of Patent: *Dec. 18, 2018

(54) PIPETTE TIP WASHING DEVICE

(71) Applicant: GRENOVA, INC., Richmond, VA (US)

(72) Inventor: Ali Safavi, Richmond, VA (US)

(73) Assignee: GRENOVA, INC., Richmond, VA (US)

( * ) Notice: Subject to any disclaimer, the term of this patent is extended or adjusted under 35 U.S.C. 154(b) by 154 days.

This patent is subject to a terminal disclaimer.

(21) Appl. No.: 15/189,750

(22) Filed: Jun. 22, 2016

(65) Prior Publication Data

US 2016/0296651 A1    Oct. 13, 2016

Related U.S. Application Data

(63) Continuation of application No. 14/266,330, filed on Apr. 30, 2014, now Pat. No. 9,421,289.
(Continued)

(51) Int. Cl.
*B08B 7/00* (2006.01)
*A61L 2/10* (2006.01)
(Continued)

(52) U.S. Cl.
CPC ............ *A61L 2/10* (2013.01); *A47L 15/0007* (2013.01); *A47L 15/0015* (2013.01);
(Continued)

(58) Field of Classification Search
CPC ............ G01N 35/1004; A47L 15/4242; A47L 15/4214; A47L 15/0084; A47L 15/0015;
(Continued)

(56) References Cited

U.S. PATENT DOCUMENTS

| 2,548,363 A | 4/1951 | Gray |
| 5,325,609 A | 7/1994 | Wells |

(Continued)

FOREIGN PATENT DOCUMENTS

| EP | 0919282 A1 | 6/1999 |
| WO | 2013064862 A1 | 5/2013 |

OTHER PUBLICATIONS

International Search Report and Written Opinion for PCT Appl. No. PCT/US2017/016821, dated Apr. 13, 2017, 12 pages.
(Continued)

*Primary Examiner* — Alexander Markoff
(74) *Attorney, Agent, or Firm* — Patent Law of Virginia, PLLC; Brian J. Teague

(57) ABSTRACT

A washing device comprises top, middle, and bottom compartments. The top compartment comprises a manifold dispenser that comprises at least one liquid input and a plurality of liquid outputs that operably direct fluid to contact a plurality of laboratory consumables held by a rack. A number of liquid outputs is equal to a number of laboratory consumables such that each one of the fluid outputs operably directs fluid at a corresponding one of the laboratory consumables. The middle compartment is positioned below the top compartment and comprises a washing chamber capable of receiving fluid output by the plurality of liquid outputs. The washing chamber has a floor comprising a material transparent to ultraviolet light. The bottom compartment is positioned below the washing chamber and has a light source that is capable of outputting UV light in the direction of the washing chamber and through the floor of the washing chamber.

17 Claims, 22 Drawing Sheets

Related U.S. Application Data

(60) Provisional application No. 61/890,523, filed on Oct. 14, 2013, provisional application No. 61/817,715, filed on Apr. 30, 2013.

(51) Int. Cl.

| | |
|---|---|
| *A47L 15/42* | (2006.01) |
| *B08B 3/08* | (2006.01) |
| *B08B 7/04* | (2006.01) |
| *B08B 9/032* | (2006.01) |
| *G01N 35/10* | (2006.01) |
| *A61L 2/00* | (2006.01) |
| *A61L 9/00* | (2006.01) |
| *A47L 15/00* | (2006.01) |

(52) U.S. Cl.
CPC ....... *A47L 15/0084* (2013.01); *A47L 15/4214* (2013.01); *A47L 15/4242* (2013.01); *A61L 2/00* (2013.01); *A61L 9/00* (2013.01); *B08B 3/08* (2013.01); *B08B 7/0057* (2013.01); *B08B 7/04* (2013.01); *B08B 9/0321* (2013.01); *G01N 35/1004* (2013.01); *A61L 2202/11* (2013.01); *A61L 2202/17* (2013.01)

(58) Field of Classification Search
CPC ..... A47L 15/0007; B08B 7/04; B08B 9/0321; B08B 7/0057; B08B 3/08; A61L 2/10; A61L 2/00; A61L 9/00; A61L 2202/17; A61L 2202/11
See application file for complete search history.

(56) References Cited

U.S. PATENT DOCUMENTS

| | | | |
|---|---|---|---|
| 5,525,302 A | | 6/1996 | Astle |
| 6,724,608 B2 | | 4/2004 | Hensley et al. |
| 7,017,594 B2 | | 3/2006 | Kurunczi |
| 7,094,314 B2 | | 8/2006 | Kurunczi |
| 7,300,525 B2 | | 11/2007 | Furst |
| 7,367,344 B2 | | 5/2008 | Kurunczi |
| 8,021,611 B2 | | 9/2011 | Roach |
| 8,367,022 B2 | | 2/2013 | Warhurst et al. |
| 8,372,356 B2 | | 2/2013 | Warhurst et al. |
| 9,421,289 B2 | * | 8/2016 | Safavi ................. A47L 15/4242 |
| 9,744,570 B2 | * | 8/2017 | Safavi ................. B08B 9/0321 |
| 2002/0063954 A1 | | 5/2002 | Horton, III |
| 2005/0074363 A1 | | 4/2005 | Dunfee |
| 2006/0054188 A1 | | 3/2006 | Gifford |
| 2006/0093530 A1 | | 5/2006 | Ueda |
| 2006/0191893 A1 | | 8/2006 | Weinfield |
| 2006/0233669 A1 | | 10/2006 | Panzer |
| 2009/0032064 A1 | * | 2/2009 | Gifford ................... B08B 3/044 134/18 |
| 2009/0301530 A1 | | 12/2009 | Shin et al. |
| 2010/0037919 A1 | | 2/2010 | Doebelin et al. |
| 2011/0306051 A1 | | 12/2011 | Belz |
| 2014/0318574 A1 | * | 10/2014 | Safavi ................. A47L 15/4242 134/1 |
| 2015/0314341 A1 | * | 11/2015 | Safavi ................. B01L 3/0275 134/1 |

OTHER PUBLICATIONS

TipCharger V20.06 User's Guide, IonField Systems, May 2013, 32 pages.
TipCharger Plasma Treatment System brochure, IonField Systems, undated, 4 pages.
PCT International Search Report and Written Opinion for PCT/US2014/036186, dated Aug. 5, 2014, 8 pages.
Product flyer, VIAFLO 96 and VIAFLO 384—Handheld 96- and 384-channel pipette, Integra Biosciences Corp., 6 pages, undated.

* cited by examiner

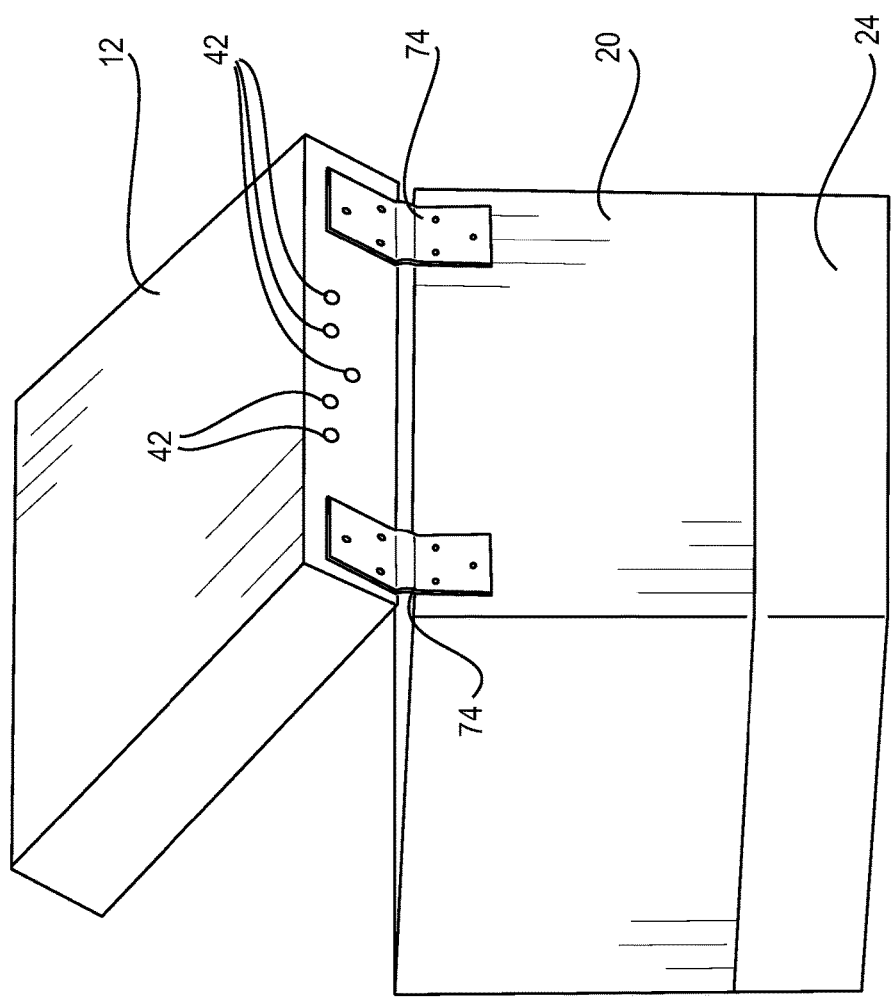

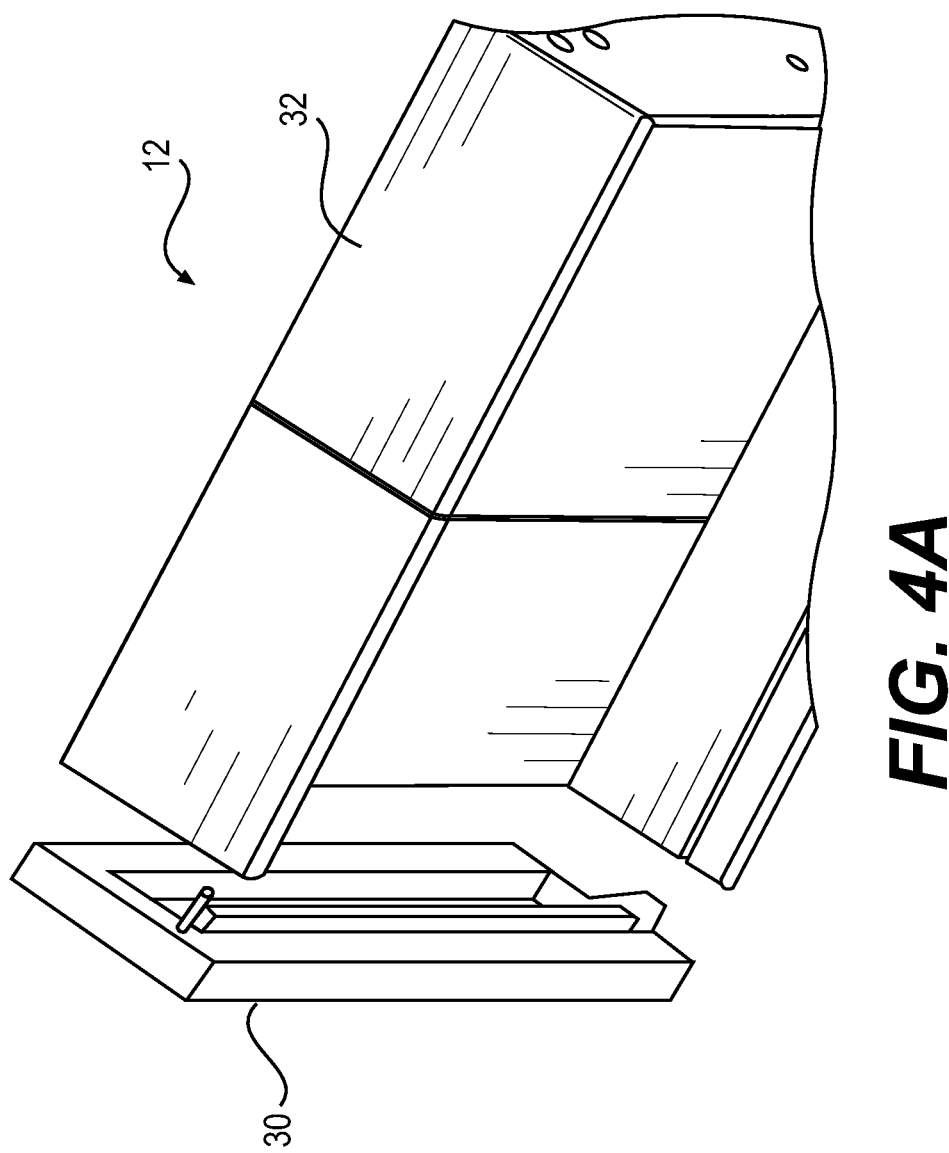

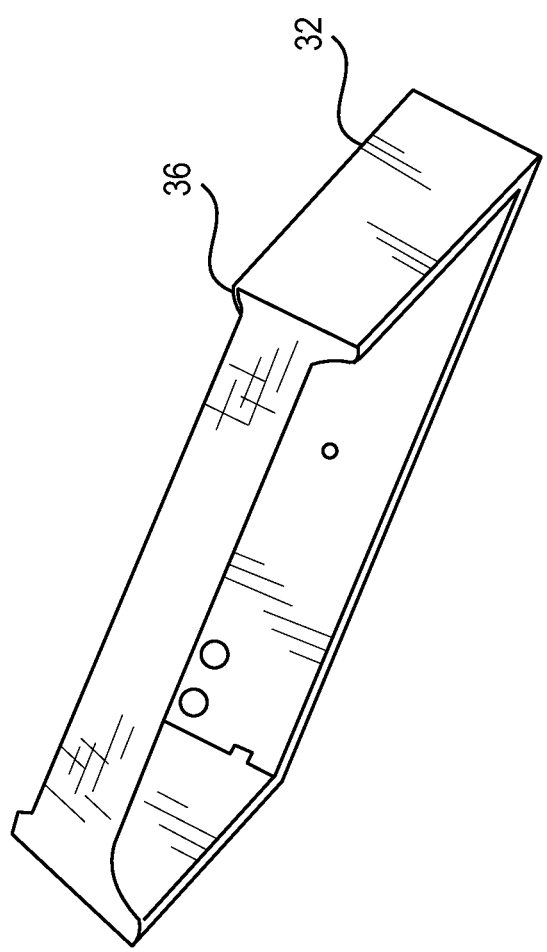

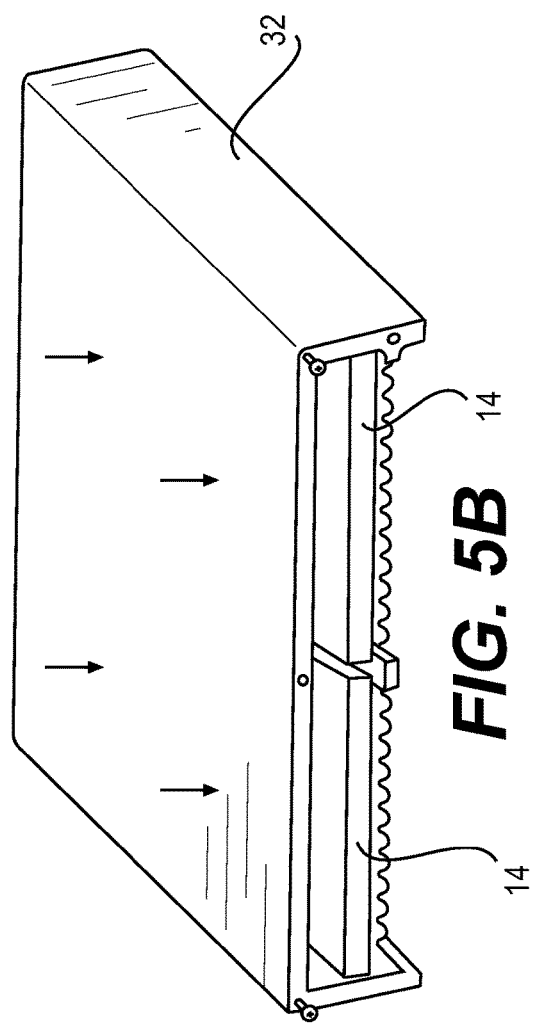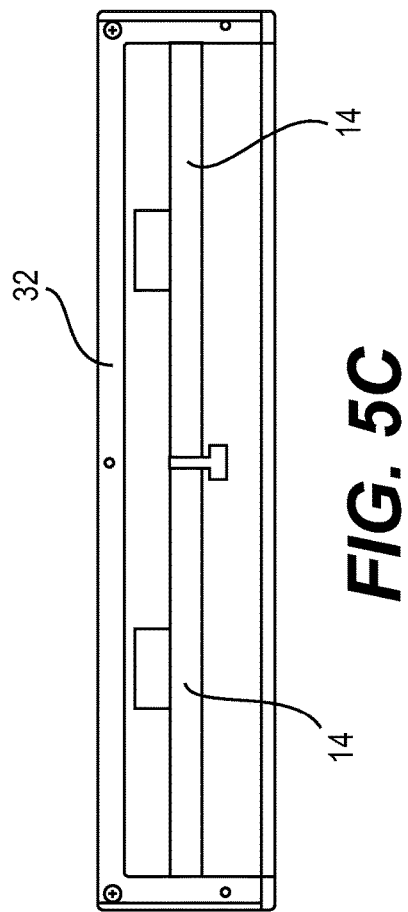
FIG. 5B
FIG. 5C

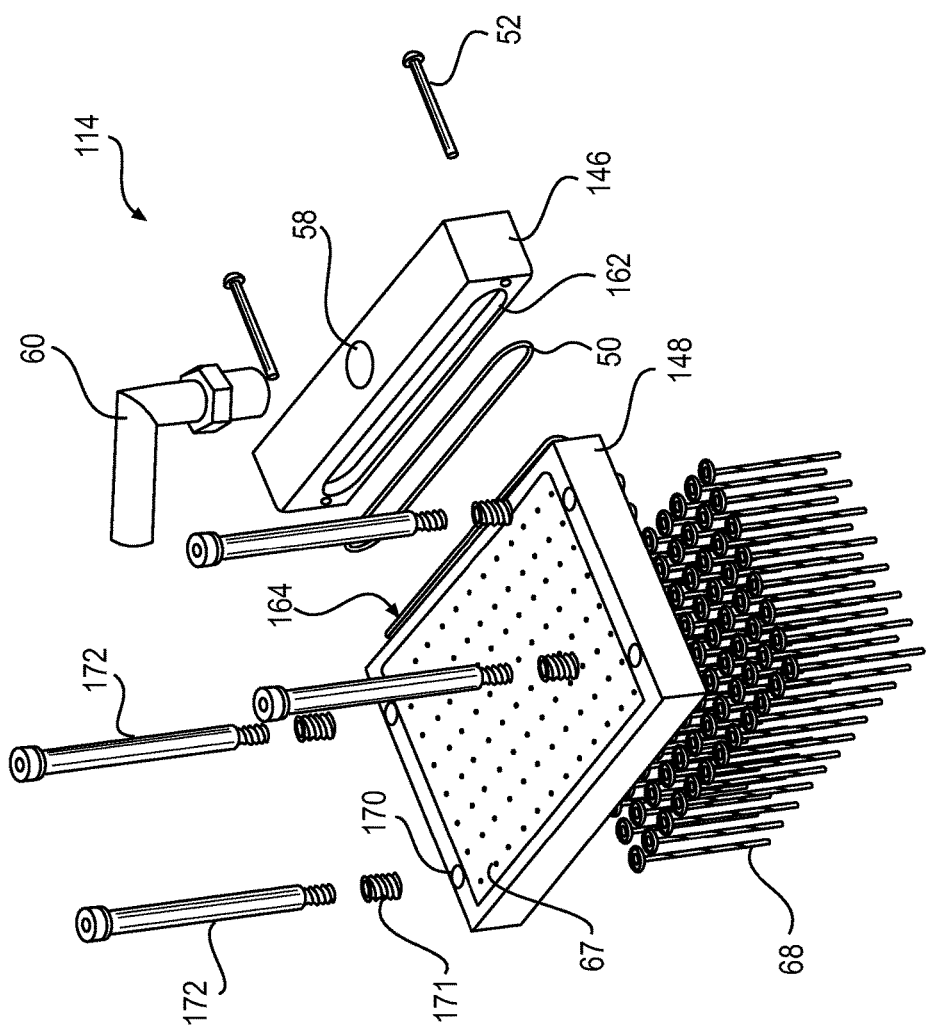

PIPETTE TIP WASHING DEVICE

CROSS-REFERENCE TO RELATED APPLICATIONS

This application is a continuation of and claims priority to U.S. patent application Ser. No. 14/266,330, filed Apr. 30, 2014, which in turn claims the benefit of U.S. Provisional Patent Application Ser. No. 61/817,715, filed Apr. 30, 2013 and U.S. Provisional Patent Application Ser. No. 61/890,523, filed Oct. 14, 2013, each of which is hereby incorporated by reference in its entirety.

FIELD OF THE INVENTION

The present technology relates to a washing device and a method of washing laboratory consumables, and more particularly to a pipette tip washing device and a method of washing pipette tips.

BACKGROUND

Every year around 4,000,000 pounds of plastic pipette tips, after a single use, are disposed of in landfills globally, leading to significant environmental pollution and costs. A typical laboratory consumes several thousand pipette tips daily for samples and assay procedures. Due to the lack of options for cleaning plastic consumables, the labs discard pipette tips after each use. Such high consumption of plastic tips adds $25,000-$1.5M to the annual operation cost to each of the approximately 14,000 research laboratories in the US.

Devices that are capable of efficient pipette tip cleaning and sterilization could save businesses substantial amounts of money in their scientific operations and drastically reduce the amount of waste produced in the course of operations. Few devices have been developed for this purpose to date. In some cases, laboratories have developed small-scale cleaning methods to reuse a few pipette tips, such as single 96-tip cases. In some small-scale automatic liquid handling instruments, there are setups for the cleaning of tips with solutions. Neither of these options, however, is large enough in scale to be useful in a large industrial, government, or academic laboratory that may use hundreds of pipette tips every day. Additionally, labs must have absolute confidence that a cleaning system has completely removed all contaminants from the pipette tips so that there is no carryover, a term for the contamination presented into an experiment by equipment used in a prior experiment.

A reusable pipette tip cleaning system that uses plasmas generated above and injected through the pipette tips is disclosed in U.S. Pat. No. 8,366,871, which is hereby incorporated herein by reference in its entirety. The plasma reaches both the inside and the outside of the tip body. However, this plasma system is expensive and requires exotic equipment to produce and direct plasmas through the pipette tips. Another cleaning system is disclosed in U.S. Pat. No. 7,300,525, which is hereby incorporated herein by reference in its entirety. This cleaning system, however, involves a complex system for the cleaning of pipette probes and stirrers. This device is designed with only a single washing cavity combining multiple jet streams. There is no application to pipette tips or a design that fosters a multiplicity of cleaning units operated simultaneously.

Thus, there is a need for a large-scale and economical method for the comprehensive cleaning and sterilization of pipette tips so they may be reused in large-scale laboratory processes.

BRIEF SUMMARY

In one embodiment of the invention, a washing device comprises a top, middle, and bottom compartment. The top compartment comprises a manifold dispenser. The manifold dispenser comprises at least one liquid input and a plurality of liquid outputs that operably direct fluid to contact a plurality of laboratory consumables held by a rack. A number of liquid outputs is equal to a number of laboratory consumables such that each one of the fluid outputs operably directs fluid at a corresponding one of the laboratory consumables. The middle compartment is positioned below the top compartment and comprises a washing chamber capable of receiving fluid output by the plurality of liquid outputs of the manifold dispenser. The washing chamber has a floor comprising a material transparent to ultraviolet (UV) light. The bottom compartment is positioned below the washing chamber. The bottom compartment has a light source mounted thereto. The light source is capable of outputting UV light in the direction of the washing chamber and through the floor of the washing chamber.

The rack may comprise a tip rack and the plurality of laboratory consumables may comprise a plurality of pipette tips. The tip rack may be configured to hold 24, 48, 96, 384, or 1536 pipette tips.

The washing chamber may be capable of retaining liquid output by the plurality of liquid outputs such that the liquid cannot enter the bottom compartment.

The washing chamber may further comprise a waste drain operable to dispense retained liquid from the wash chamber.

The top compartment may further comprise a plurality of manifold dispensers, each manifold dispenser comprising at least one liquid input and a plurality of liquid outputs that operably direct fluid to contact a plurality of laboratory consumables held by a respective rack. A number of liquid outputs of each manifold dispenser may be equal to a number of laboratory consumables held by a respective rack such that each one of the fluid outputs operably directs fluid at a corresponding one of the laboratory consumables.

The material transparent to UV light may comprise quartz glass.

The device may further comprise a plurality of fiber optic channels extending through the manifold dispenser at each of the plurality of liquid outputs. The light source may be further coupled to the plurality of fiber optic channels. The plurality of liquid outputs each may comprise a nozzle having an opening into which one of the plurality of fiber optic channels extends.

The wash compartment may be further configured to removably receive a wash sleeve, the wash sleeve comprising a material capable of reflecting at least a portion of the UV light output by the light source.

The washing chamber may have a plurality of walls and one or more of the plurality of walls comprise a material transparent to ultraviolet (UV) light. The middle compartment may include one or more additional light sources mounted thereto and proximate to one or more of the plurality of walls of the washing chamber. The one or more additional light sources may be capable of outputting UV light in the direction of the washing chamber and through one or more of the plurality of walls of the washing chamber.

The device may further comprise one or more transducers capable of outputting sound in an ultrasonic range into the washing chamber.

The device may further comprise one or more mechanical cylinders that operably agitate the rack.

The middle compartment may further comprise a drawer capable of opening and closing.

The manifold dispenser may be capable of being raised and lowered vertically relative to the middle compartment In addition to the washing device, as described above, other aspects of the present invention are directed to corresponding methods for washing laboratory consumables.

BRIEF DESCRIPTION OF THE SEVERAL VIEWS OF THE DRAWING(S)

The foregoing summary, as well as the following detailed description of the disclosure, will be better understood when read in conjunction with the appended drawings. For the purpose of illustrating the disclosure, there are shown in the drawings embodiments which are presently preferred. It should be understood, however, that the disclosure is not limited to the precise arrangements and instrumentalities shown. In the drawings:

FIGS. 3A and 3B are front and rear perspective views of the exemplary pipette tip washing device of the present disclosure with the top compartment in an open position.

FIG. 4A is a perspective view of a top compartment of the pipette tip washing device illustrated in FIG. 1.

FIG. 4B is a perspective view of a receiving compartment of the top compartment illustrated in FIG. 4A.

FIG. 5A-5D are an exploded perspective view, a top perspective view, a side view, and a bottom view, respectively, of the top compartment of the pipette tip washing device and manifold dispensers configured to be located in the top compartment.

Figure 1A:
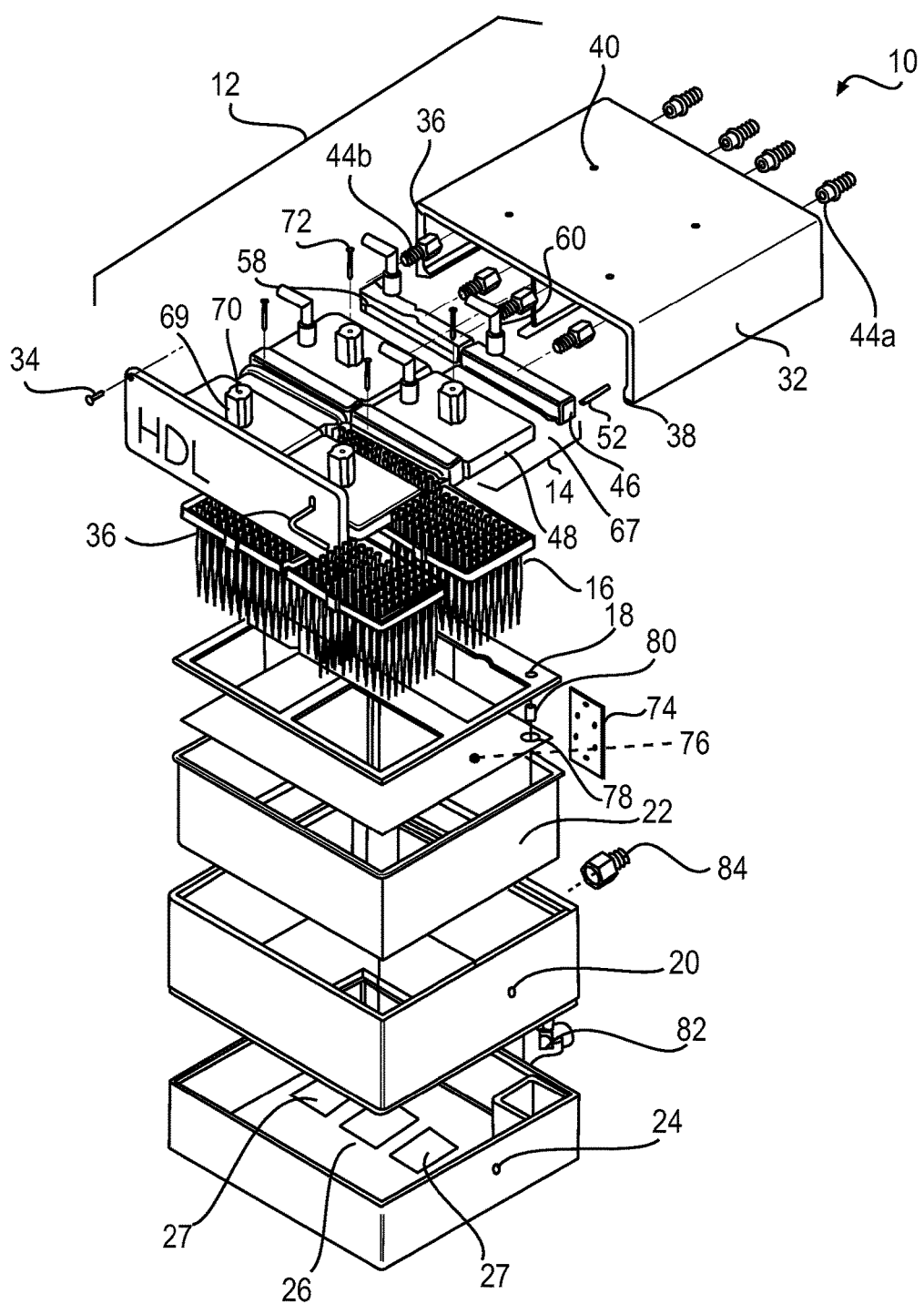
FIGS. 1A and 1B are exploded perspective views of an exemplary embodiment of a pipette tip washing device of the present disclosure.
Figure 1B:
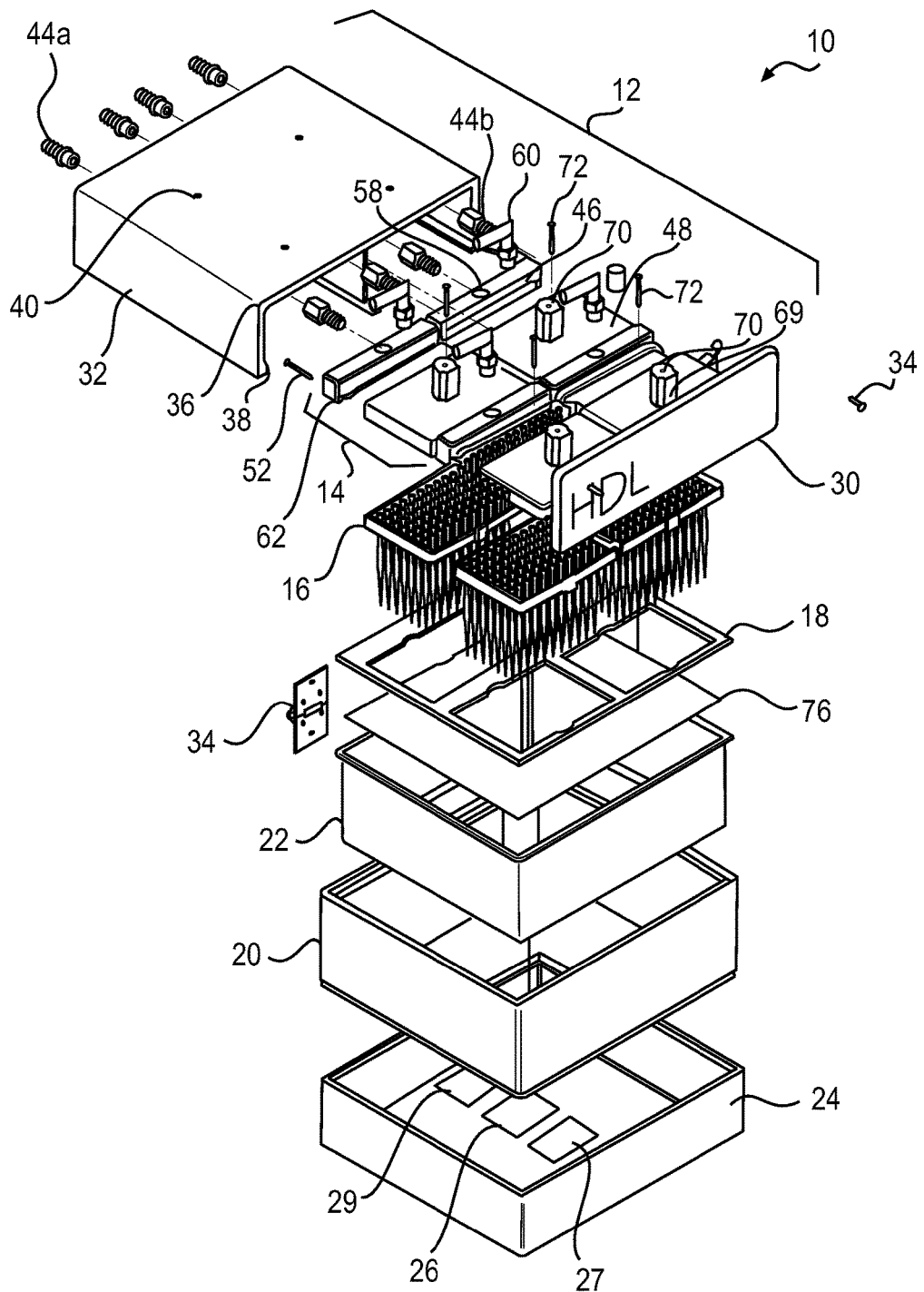
Figure 2:
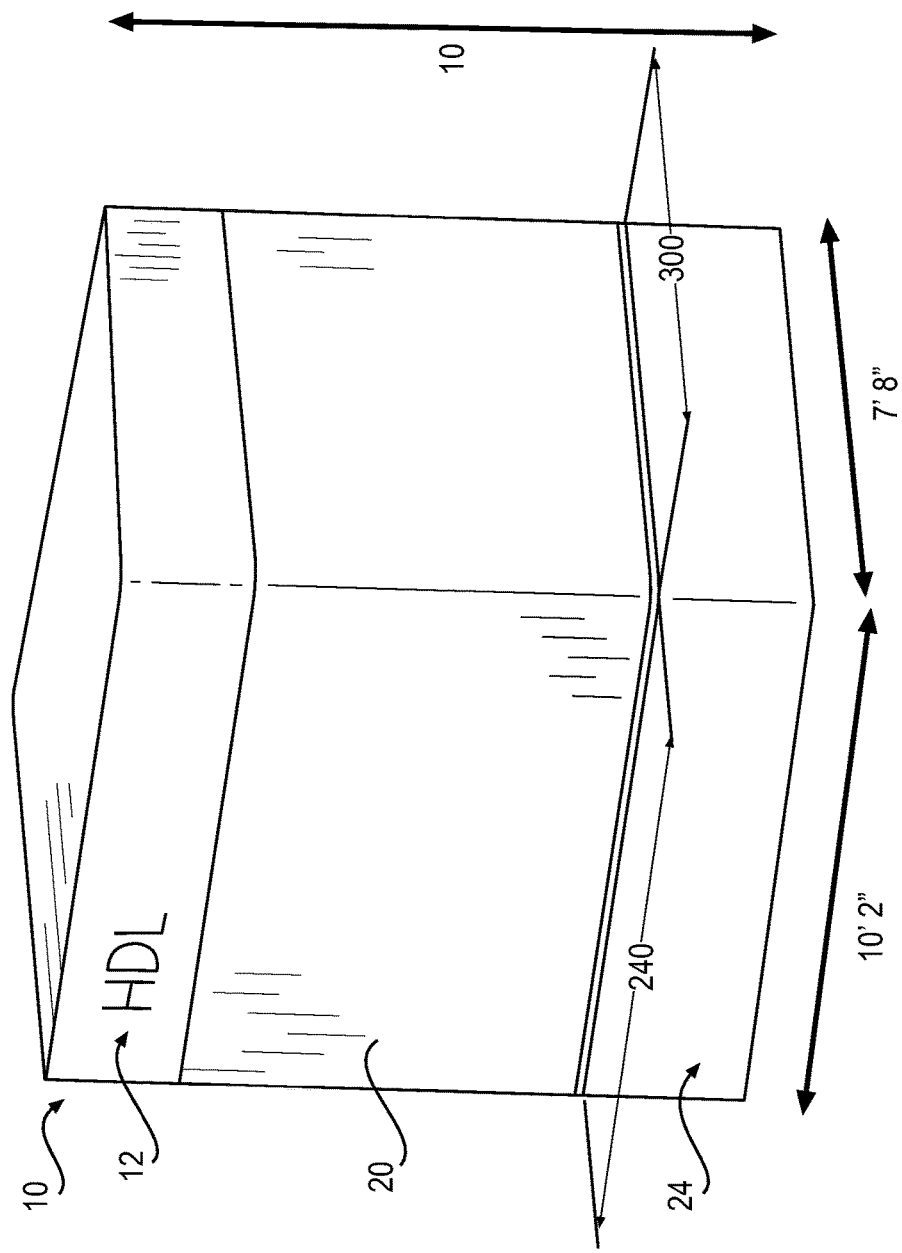
FIG. 2 is a perspective view of the exemplary pipette tip washing device of the present disclosure.
Figure 3A:
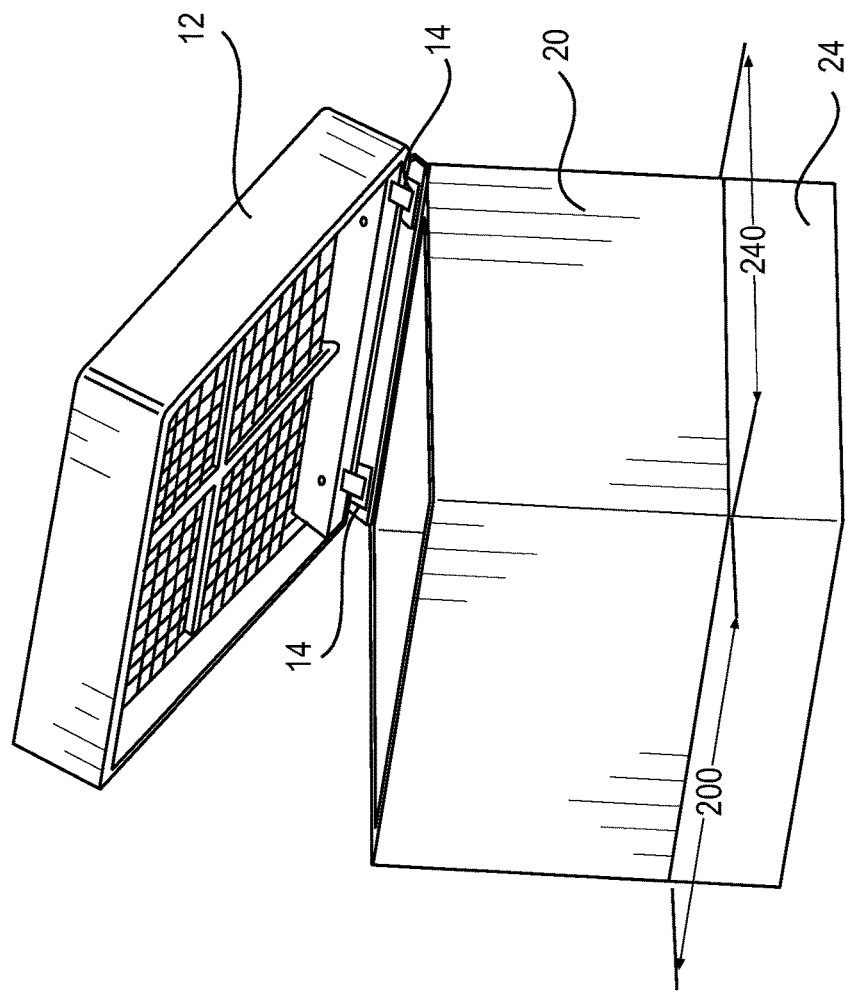
Figure 5A:
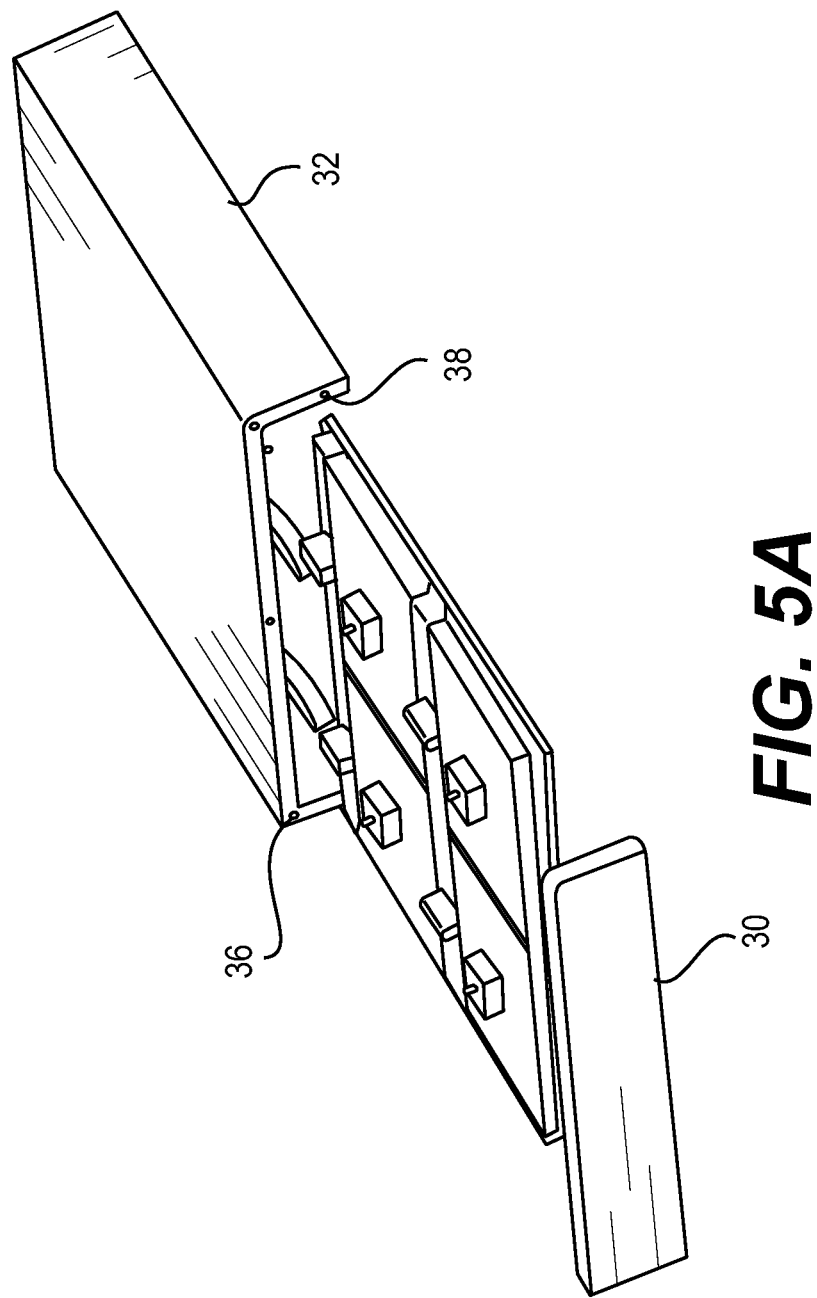
Figure 5D:
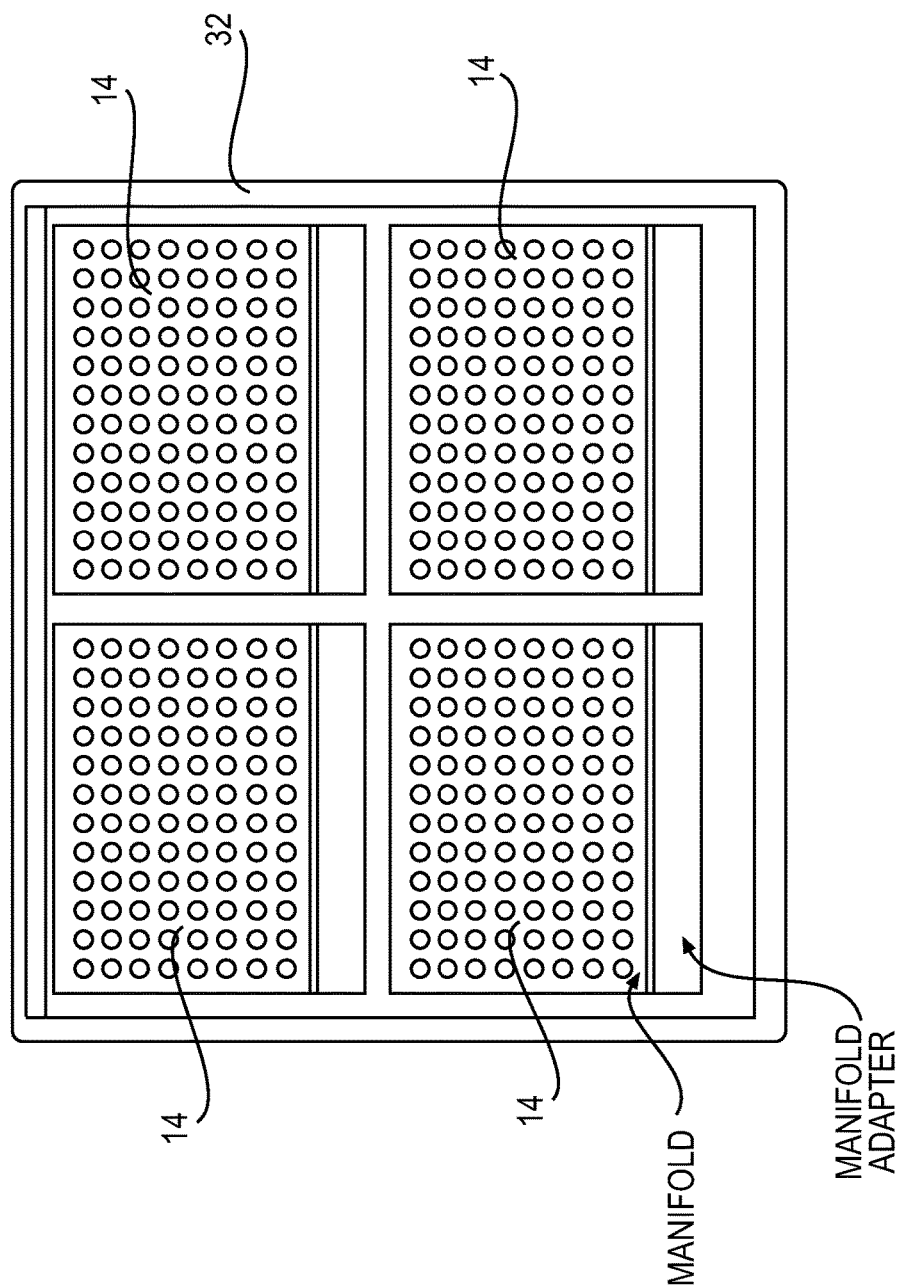
Figure 6A:
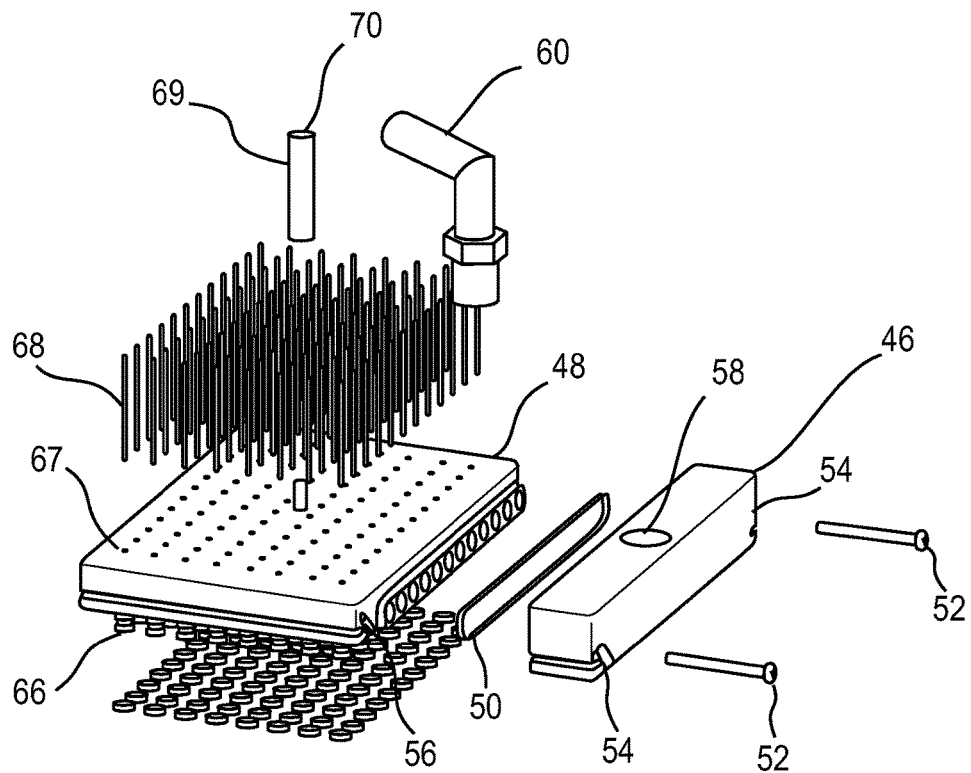
FIG. 6A is an exploded perspective view of a manifold dispenser of the present invention.
Figure 6B:
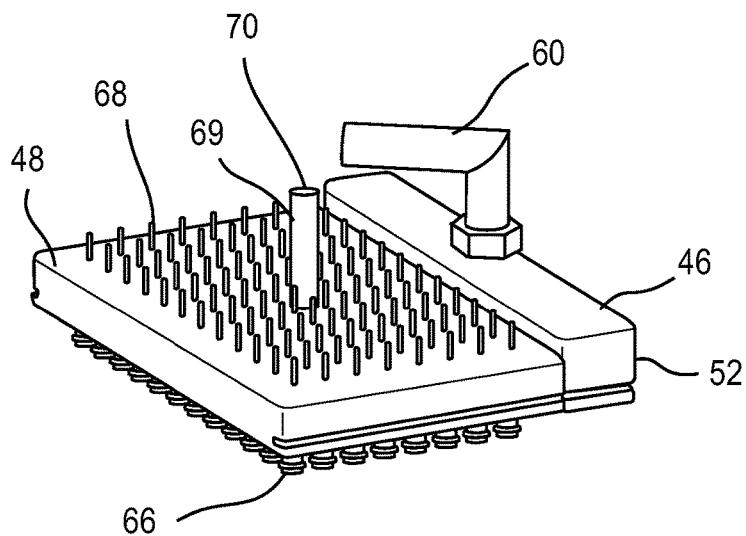
FIG. 6B is a top perspective view of the manifold dispenser of the present invention.
Figure 6C:
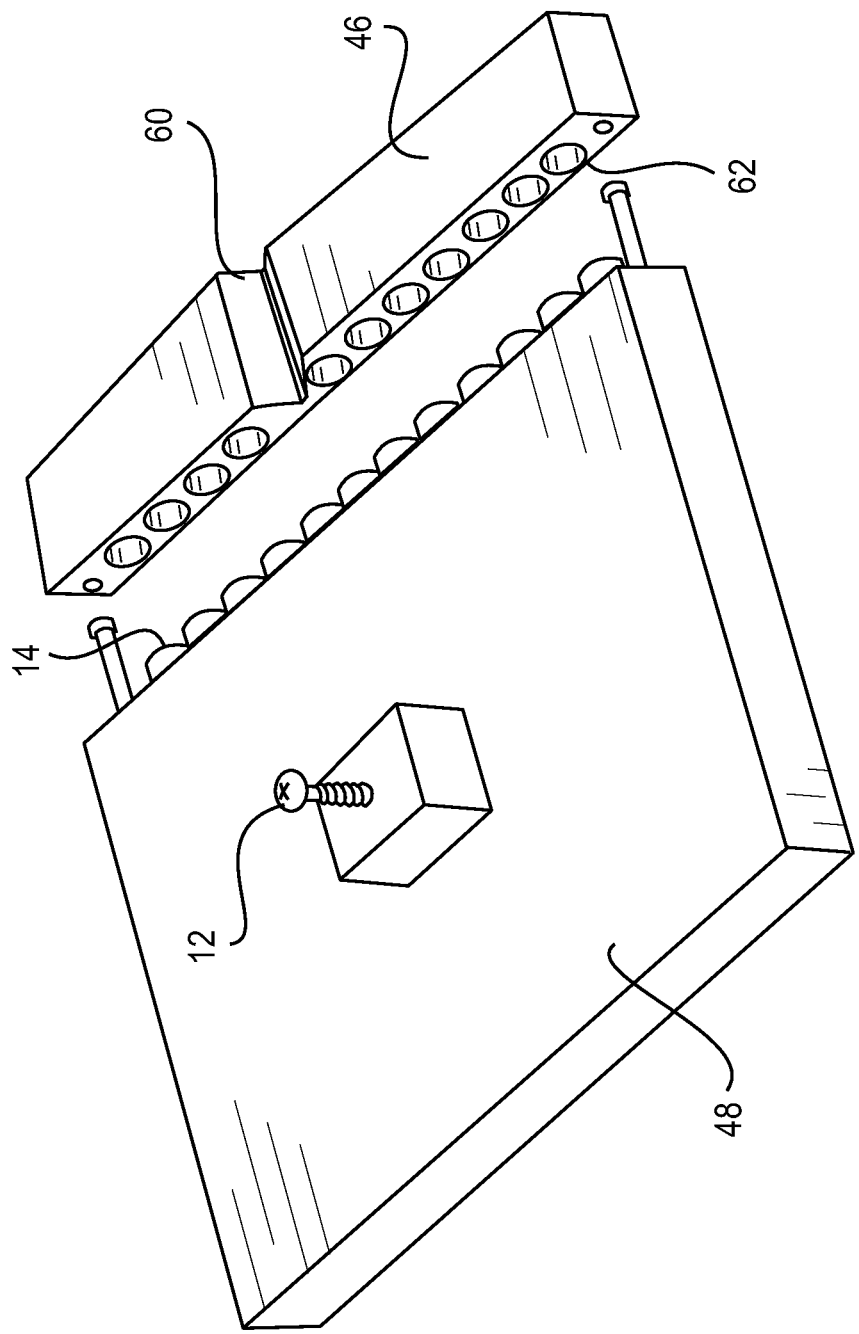

FIG. 6C an exploded view of a manifold dispenser of the present invention.

Figure 6D:
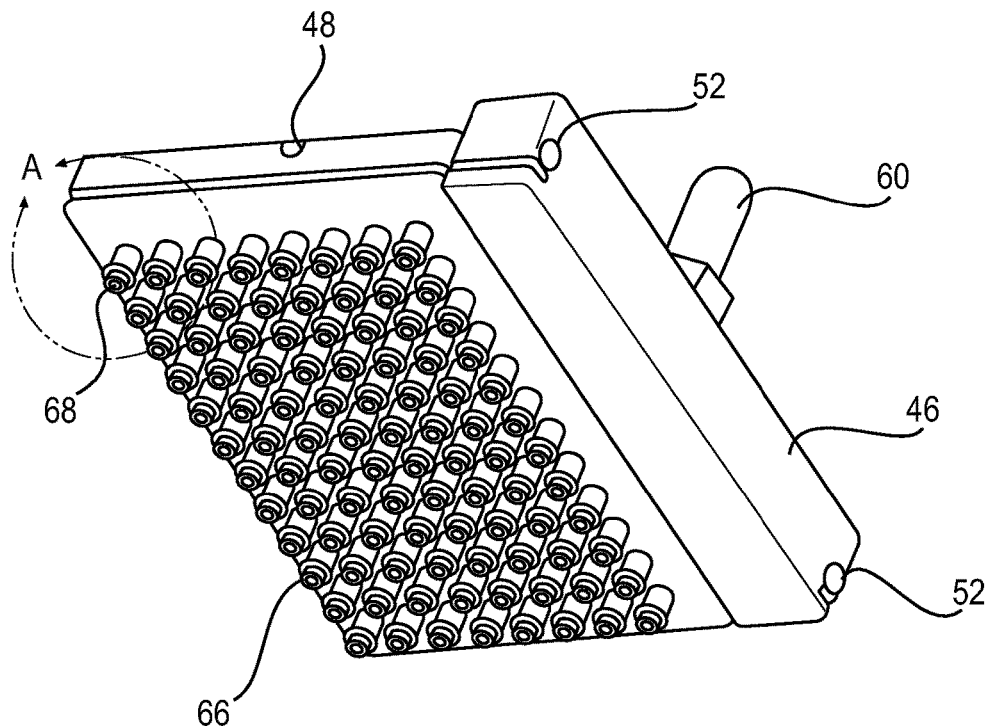

FIG. 6D is a bottom perspective view of the manifold dispenser of the present invention.

Figure 6E:
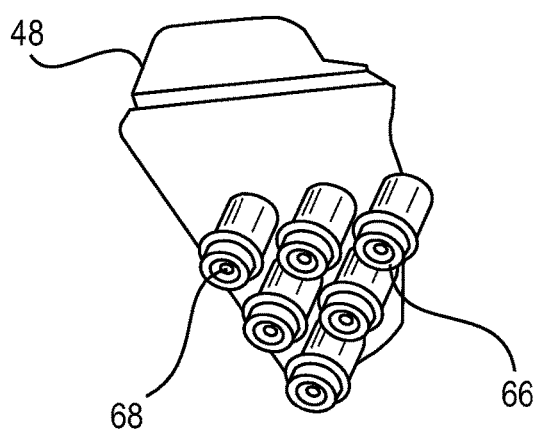

FIG. 6E is a magnified view of portion A of the manifold dispenser illustrated in FIG. 6D.

Figure 7B:
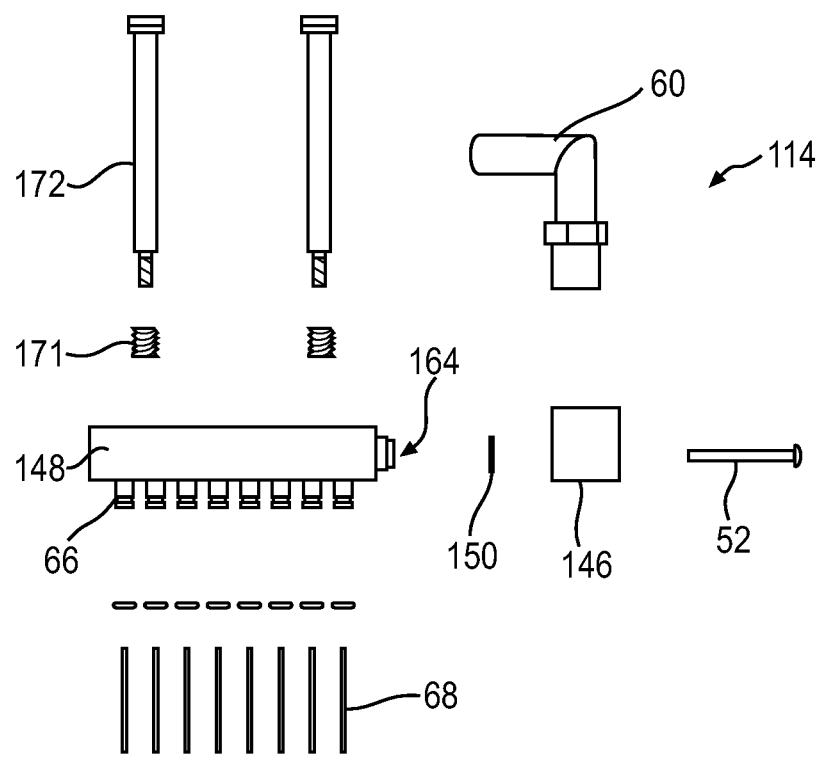

FIGS. 7A and 7B are an exploded perspective view and an exploded side view of another embodiment of the manifold dispenser of the present invention.

Figure 8A:
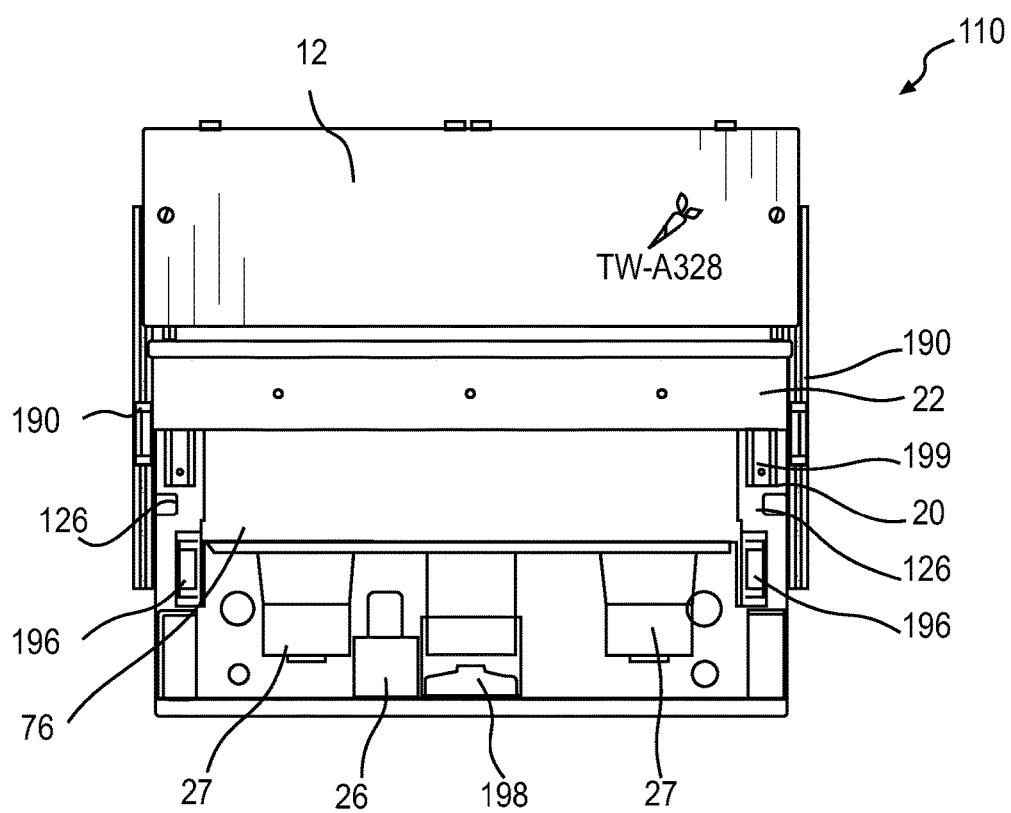
Figure 8B:
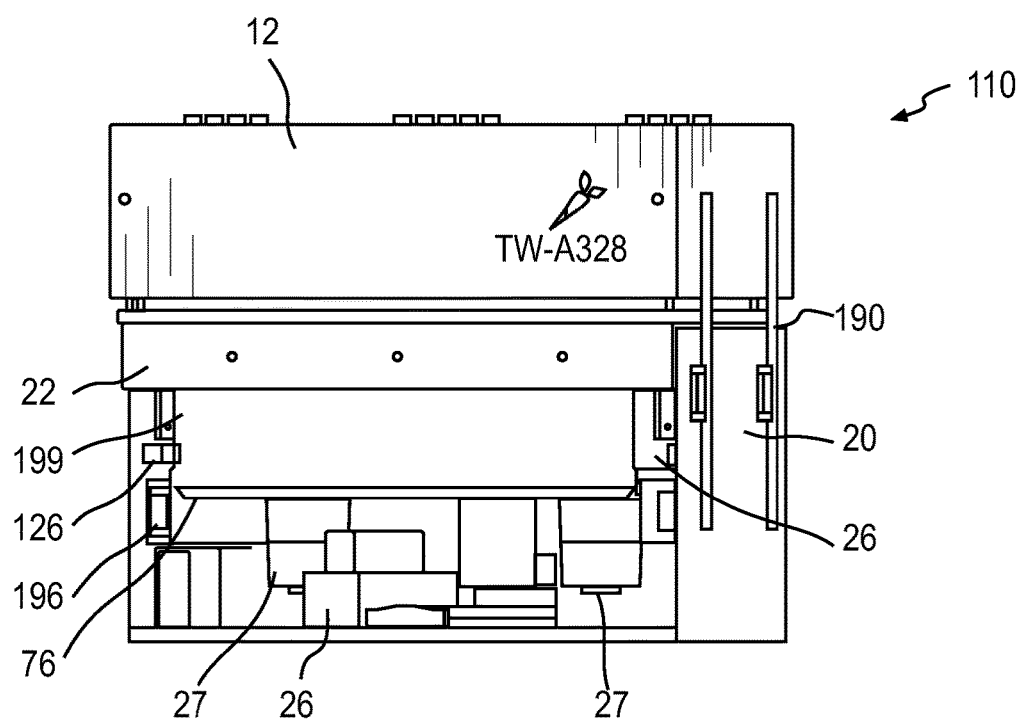

FIGS. 8A and 8B are partial phantom front and perspective views of another exemplary embodiment of a pipette tip washing device of the present disclosure.

Figure 8C:
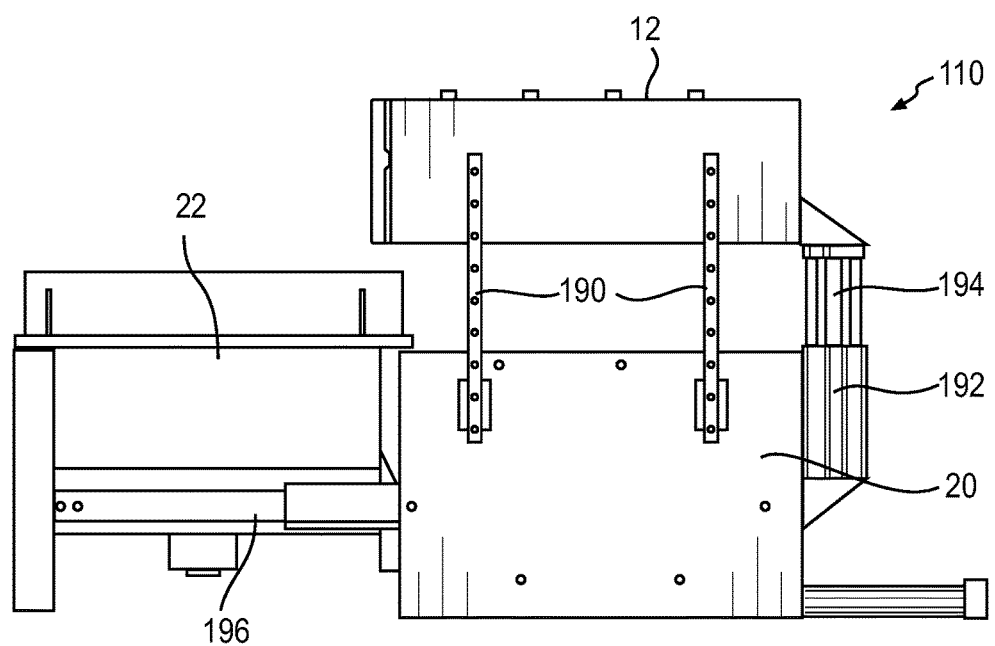

FIG. 8C is a side view of the pipette tip washing device illustrated in FIGS. 8A and 8B in an opened position.

FIGS. 9A-9D are perspective views of the pipette tip washing device illustrated in FIGS. 8A-8C in various positions during operation of the device in accordance with the present disclosure.

DETAILED DESCRIPTION

An exemplary pipette tip washing device 10 is illustrated in FIGS. 1-3B. The pipette tip washing device 10 includes a top compartment 12, manifold dispensers 14, tip racks 16, a tip rack support 18, a middle compartment 20, a wash sleeve 22, a bottom compartment 24, an ultraviolet (UV) light source 26, and optional transducers 27, although the pipette tip washing device 10 may include other elements in other configurations. This exemplary technology includes a number of advantages including providing a device and method for the efficient and economical sterilization of a large number of pipette tips for use in large scale laboratory settings.

Referring more specifically to FIGS. 4A-4B, an exemplary top compartment 12 of the exemplary pipette tip washing device 10 is shown. The top compartment 12 includes a front cover 30 removably coupled to a receiving chamber 32, although the top compartment 12 may include other elements in other configurations. Front cover 30 is constructed of stainless steel, although front cover may be constructed of other numbers and types of materials. Front cover 30 is removably coupled to the receiving chamber 32 through one or more one or more screws 34 which are inserted into holes 36 in the receiving chamber 32, although other attachment methods may be utilized to removably couple front cover 30 to receiving chamber 32.

Receiving chamber 32 is configured to receive the one or more manifold dispensers 14 as illustrated in FIGS. 5A-5D. In this example, receiving chamber 32 is configured to receive four manifold dispensers 14, although receiving chamber 32 may receive other numbers of manifold dispensers 14 in other configurations. In this example, the receiving chamber 32 includes internal rails 38 on the sidewalls which support the manifold dispensers 14 and one or more holes 40 disposed on the top surface of the receiving chamber 32 configured to receive screws for secure attachment to the manifold dispensers 14, although the receiving chamber 32 may include other elements in other locations to support and securely attach the manifold dispensers 14 within the receiving chamber 32.

Referring again to FIGS. 1A and 1B, the receiving chamber 32 further includes one or more input ports 42 configured to receive liquid input fittings 44a and 44b, which are disposed on opposite sides of the wall of the receiving chamber 32 and are configured to receive liquid into the pipette tip washing device 10 from an external control source (not shown). The external control source may include a pump, control valves, and electronics necessary to deliver wash liquids to the pipette tip washing device 10 in accordance with the present technology. The receiving chamber 32 is constructed of stainless steel, although the receiving chamber 32 may be constructed of other numbers and types materials.

Referring now to FIGS. 6A-6E, an exemplary manifold dispenser 14 is shown. The manifold dispenser is configured to be inserted into receiving compartment 32. The manifold dispenser 14 includes a manifold adapter 46 which may be coupled to a manifold body portion 48, and an O-ring adapter 50, although the manifold dispenser 14 may include other elements in other configurations. In this exemplary manifold dispenser 14, the manifold adapter 46 is coupled to the manifold body portion 48 by screws 52 which are configured to be inserted into the holes 54 and 56 in the manifold adapter 46 and the manifold body portion 48, respectively, although other attachment mechanisms may be utilized. The O-ring adapter 50 is located at the contact point between the manifold adapter 46 and the manifold body portion 48 to provide a watertight seal when the manifold adapter 46 and the manifold body portion 48 are coupled together.

The manifold adapter 46 includes a liquid input 58 configured to receive a manifold elbow input 60 which may be coupled to the liquid input fittings 44b, as illustrated in FIG. 1, to transfer liquid into the manifold adapter 46, although other liquid input ports in other configurations may be utilized to introduce liquid into the manifold adapter 46. The manifold adapter 46 also includes exit ports 62, as illustrated in FIG. 6C, which are coupled to the manifold body portion 48 to transfer liquid from the manifold adapter 46 to the manifold body portion 48. The manifold adapter 46 is constructed of a chemical resistant material such as, by way of example only, polyphenylene sulfide or polyetheretherketone (PEEK), although the manifold adapter 46 may be constructed of other types and numbers of materials.

The manifold body portion 48 includes input ports 64 which are configured to be aligned with the exit ports 62 of the manifold adapter 46 when the manifold adapter 46 and the manifold body portion 48 are coupled. The input ports 64 receive liquid transferred from the manifold adapter 46. The manifold body portion 48 also includes a plurality of liquid outputs 66 configured to operably direct fluid introduced into the manifold dispenser 14 from the manifold body portion 48 into to the wash sleeve 22 to contact a number of laboratory consumables, such as pipette tips. In this example, the liquid outputs 66 are nozzles extending from the manifold body portion 48, although other types of liquid outputs may be utilized in other configurations. The number of liquid outputs 66 in the manifold body portion 48 may match the number of pipette tips in the tip rack 16, which are held below the manifold body portion 48, as illustrated in FIG. 1. By way of example, the manifold body portion 48 may include 96 liquid outputs 66, although manifold body portion 48 may include other numbers of liquid outputs 66 configured for use with different tip racks 16.

Manifold body portion 48 may further optionally include a number of holes 67 in the surface opposite to the liquid outputs 66, the holes 67 being configured to receive fiber optic needles 68. The fiber optic needles 68 extend through the manifold body portion 48 and extend into liquid outputs 66 to direct light into the wash sleeve 22. In one example, the fiber optic needles 68 are attached to the UV-light source 26 to direct UV-light to the wash sleeve 22, although the fiber optic needles 68 may receive light from other light sources in other configurations. The manifold body portion 48 further includes a top support structure 69 including a hole 70 configured to be aligned with hole 40 in the receiving chamber 32. Screw 72 may be inserted through hole 40 in the receiving chamber 32 and hole 70 in the top support structure 68 to securely attach manifold body portion 48 to the receiving chamber 32, although other attachment mechanisms may be utilized. The manifold body portion 48 is constructed of a chemical resistant material such as, by way of example only, polyphenylene sulfide or polyetheretherketone (PEEK), although the manifold body portion 48 may be constructed of other types and numbers of materials.

FIGS. 7A and 7B illustrate another exemplary manifold dispenser 114 that may be utilized with the pipette tip washing device of the present disclosure. Manifold dispenser 114 is the same in structure and operation as the manifold dispenser 14 illustrated in FIGS. 6A-6E, except as illustrated and described herein. Like parts will be described using like reference numerals. The manifold dispenser 114 includes a manifold adapter 146 which may be coupled to a manifold body portion 148, and an O-ring adapter 50, although the manifold dispenser 114 may include other elements in other configurations. In this exemplary manifold dispenser 114, the manifold adapter 146 is coupled to the manifold body portion 148 by screws 52, although other attachment mechanisms may be utilized. The O-ring adapter 50 is located at the contact point between the manifold adapter 146 and the manifold body portion 148 to provide a seal when the manifold adapter 146 and the manifold body portion 148 are coupled together.

The manifold adapter 146 includes a liquid input 58 configured to receive a manifold elbow input 60 which may be coupled to the liquid input fittings 44b, as illustrated in FIG. 1, to transfer liquid into the manifold adapter 146, although other liquid input ports in other configurations may be utilized to introduce liquid into the manifold adapter 146. The manifold adapter 146 also includes a single exit port 162, which is coupled to the manifold body portion 148 to transfer liquid from the manifold adapter 146 to the manifold body portion 148. The manifold adapter 146 is constructed of a chemical resistant material such as, by way of example only, polyphenylene sulfide or polyetheretherketone (PEEK), although the manifold adapter 146 may be constructed of other types and numbers of materials.

The manifold body portion 148 includes an input port 164 which is configured to be aligned with the exit port 162 of the manifold adapter 146 when the manifold adapter 146 and the manifold body portion 148 are coupled. The input port 164 receives liquid transferred from the manifold adapter 146. The manifold body portion 148 also includes a plurality of liquid outputs 66 configured to operably direct fluid introduced into the manifold dispenser 114 from the manifold body portion 148 into to the wash sleeve 22 to contact a number of laboratory consumables, such as pipette tips. In this example, the liquid outputs 66 are nozzles extending from the manifold body portion 148, although other types of liquid outputs may be utilized in other configurations. The number of liquid outputs 66 in the manifold body portion 148 may match the number of pipette tips in the tip rack 16, which are held below the manifold body portion 148, as illustrated in FIG. 1. By way of example, the manifold body portion 148 may include 96 liquid outputs 66, although manifold body portion 148 may include other numbers of liquid outputs 66 configured for use with different tip racks 16.

Manifold body portion 148 may further optionally include a number of holes 67 in the surface opposite to the liquid outputs 66, the holes 67 being configured to receive fiber optic needles 68. The fiber optic needles 68 extend through the manifold body portion 148 and extend into liquid outputs 66 to direct light into the wash sleeve 22. In one example, the fiber optic needles 68 are attached to the UV-light source 26 to direct UV-light to the wash sleeve 22, although the fiber optic needles 68 may receive light from other light sources in other configurations. In this embodiment, the manifold body portion 148 further includes holes 170 configured to receive springs 171. The springs 171 are configured to receive shoulder bolts 172 to attach the manifold body portion 148 to the receiving compartment 32, although other attachment mechanisms may be utilized. The springs 171 allow a range of movement of manifold body portion 148 to provide alignment with the pipette tips prior to washing. The manifold body portion 148 is constructed of a chemical resistant material such as, by way of example only, polyphenylene sulfide or polyetheretherketone (PEEK), although the manifold body portion 48 may be constructed of other types and numbers of materials.

Referring again to FIGS. 1A and 1B, the pipette tip washing device 10 includes four tip racks 16 configured to be inserted into tip rack supports 18, although the pipette tip washing device 10 may include other numbers of tip racks. Although the wash device 10 is described with respect to pipette tips, it is to be understood that the present invention could be utilized with racks which hold other types of laboratory consumables, such as laboratory consumables with similar configurations to pipette tips. Further, the present technology may be utilized with pipette tips of various sizes. By way of example 1, 2, 8, 16 or more tip racks 16 may be utilized for maximization of the throughput in the space available in the receiving compartment 32. In this example, the tip racks 16 hold 96 pipette tips for a total of 384 pipette tips in the pipette tip washing device, although the tip racks 16 may hold other numbers of pipette tips, or other laboratory consumables. The tip rack supports 18 support the tip racks 16 above the wash sleeve 22.

The middle compartment 20 of pipette tip washing device 10 is configured to be attached to the top compartment 12 through hinges 74 such that the top compartment 12 may be lifted in order to insert tip racks 16 into tip rack support 18, although other attachment mechanisms may be utilized to attach the middle compartment 20 to the top compartment 12. The middle compartment 20 is capable of receiving fluid output by the one or more manifold dispensers 14 such that fluid does not enter the bottom compartment 24.

The middle compartment 20 further includes a floor 76 comprising a material transparent to ultraviolet (UV) light, such as by way of example only, quartz, although other transparent materials may be utilized. Floor 76 is configured to provide a water tight-seal that prevents fluid introduced into the middle compartment 20 from entering the bottom compartment 24. Drain 78 exits the floor 76 and directs fluid through drain fitting 80. Drain fitting 80 is coupled to a waste drain elbow fitting 82. The waste drain elbow fitting 82 extends from the drain fitting 80 from the bottom of the middle compartment 20 into the bottom compartment 24 and is coupled to waste output fitting 84 which exits the pipette tip washing device 10 through the bottom compartment 24, although the drain may have other configurations. The middle compartment is further configured to receive the wash sleeve 22. The sidewalls of the middle compartment 20 are constructed of stainless steel, although the middle compartment 20 may be constructed of other numbers and types of materials.

The wash sleeve 22 or wash chamber is configured to be inserted into the middle compartment 20. The wash sleeve 22 is constructed of a material capable of reflecting at least a portion of the UV-light from the UV-light source 26, although the wash sleeve 22 may be constructed of other types and numbers of materials. In another embodiment, the wash sleeve 22 may be constructed of a transparent material, such as quartz by way of example only, in order to direct UV-light into the middle compartment 20 from other light sources, such as the light sources illustrated in FIGS. 8A and 8B below. The wash sleeve 22 is replaceable and protects the sidewalls of the middle compartment 20 from fluid.

The bottom compartment 24 is located below the middle compartment 20 and separated by floor 76. The bottom compartment 24 houses UV-light source 26, such as a UV lamp, which is configured to direct UV-light through the floor 76 into the middle compartment 20, although the UV-light compartment may include other numbers and types of light sources in other configurations. The bottom compartment 24 further may include one or more transducers 27 to direct sound in the ultrasonic range into the middle compartment 20, although other devices may be utilized to direct sound in other ranges to the middle compartment 20. The bottom compartment is easily accessible to replace the UV-light source 26. The bottom compartment 24 is protected from fluids by the floor 76. The bottom compartment 24 further includes an exit port 86 located under drain 78 in floor 76. The drain elbow fitting 82 extends from the drain fitting 80 from the bottom of the middle compartment 20 into the bottom compartment 24 and is coupled to waste output fitting 84 which exits the pipette tip washing device 10 through exit port 86 in the bottom compartment 24, although the drain may have other configurations.

Another embodiment of an exemplary pipette tip washing device 110 is illustrated in FIGS. 8A-9D. Pipette tip washing device 110 is the same in structure and operation as the pipette tip washing device 10 illustrated in FIGS. 1-3B, except as illustrated and described herein. Like parts will be described using like reference numerals. In this embodiment, top compartment 12 is coupled to middle compartment 20 by rails 190 that allow top compartment 12 to be raised vertically along the rails 190 above middle compartment 20. In one embodiment, top compartment 12 is raised in an automated process by mechanical cylinder 192 which is coupled to rod 194, as shown in FIG. 8C, although top compartment 12 may be manually raised.

In this embodiment, middle compartment 20 is disposed on telescopic guides 196 that allow the middle compartment 20 to be opened as a drawer for insertion of tip racks 16, although other devices that allow middle compartment to be opened may be utilized. Middle compartment 20 may be opened and closed in an automated process by cylinder 198, although middle compartment 20 may be opened manually as well. Middle compartment 20 further includes UV light sources 126 disposed on the inside surface thereof. The UV light sources 126 may be utilized with a transparent wash sleeve to direct light onto pipette tips held in pipette tip racks 16 during operating of the pipette tip washing device 110.

In this embodiment, the middle compartment 20 further includes mechanical cylinders 199 that may operatively raise and lower the tip racks 16 when the top compartment 12 is in an open position. The mechanical cylinders 199 may be utilized to agitate the pipette tips to improve wash quality during the wash process or to assist in the drying process.

Figure 9A:
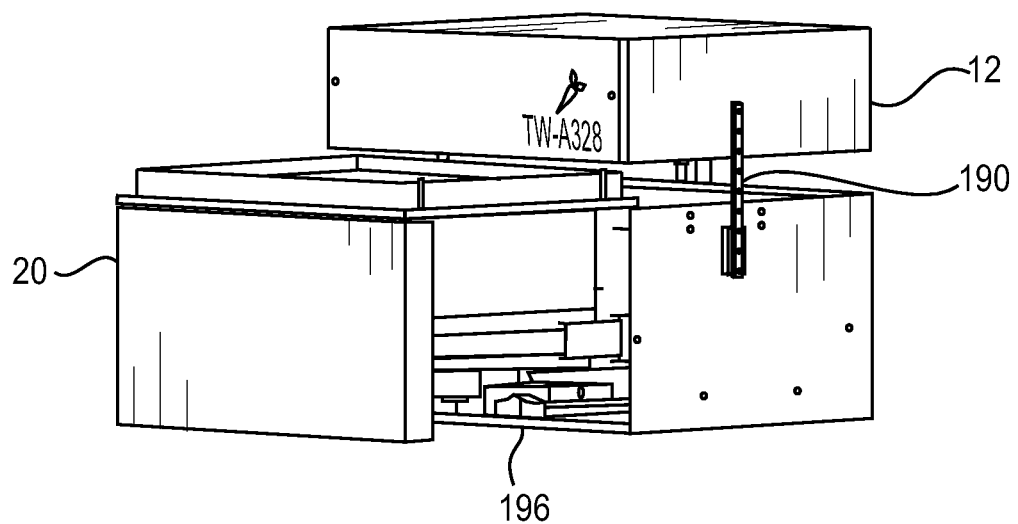
Figure 9B:
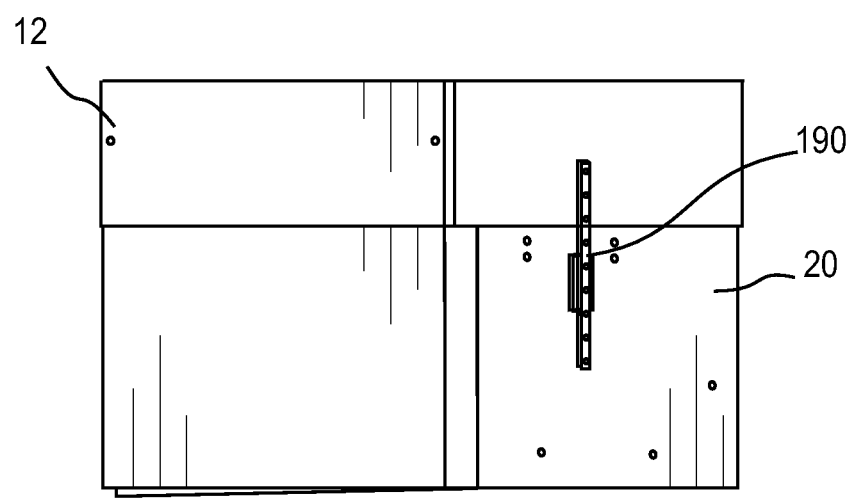
Figure 9C:
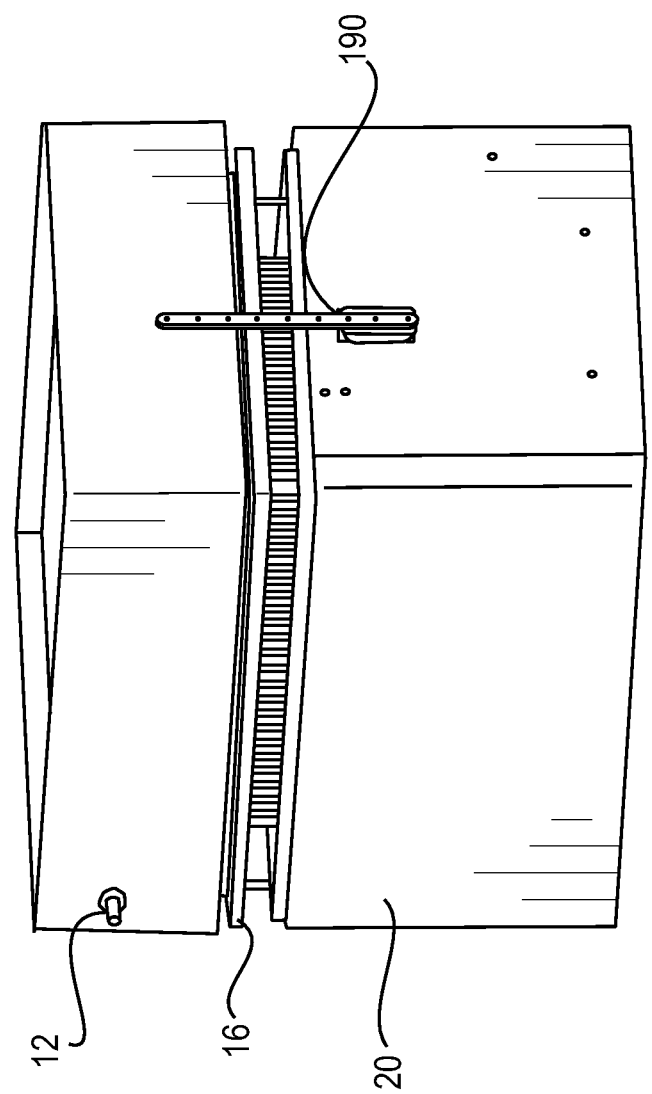
Figure 9D:
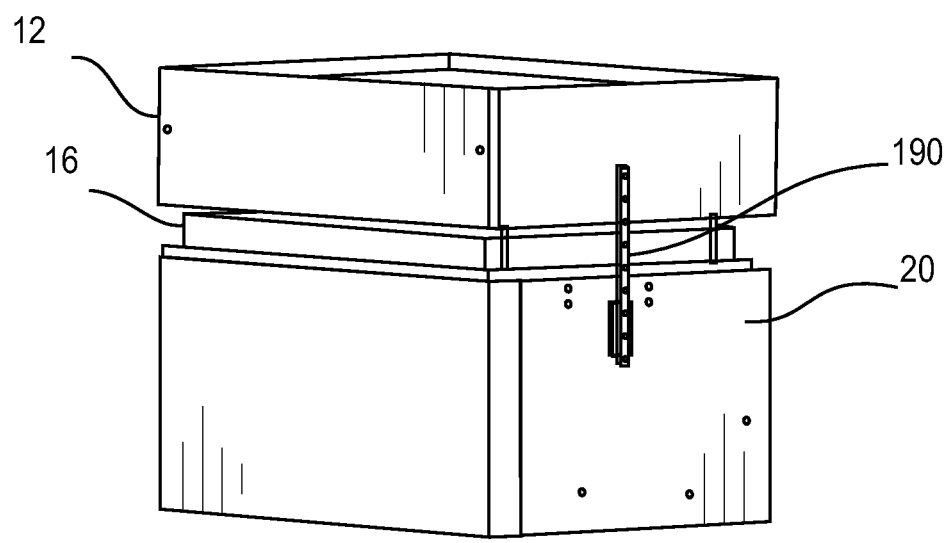

Referring now to FIGS. 9A-9D, the pipette tip washing device 110 is illustrated in various states of operation. FIG. 9A shows the pipette tip washing device 110 in an opened position with top compartment 12 raised and middle compartment 20 opened as a drawer for the insertion of pipette tips. FIG. 9B shows the pipette tip washing device 110 in the closed position for washing the pipette tips. FIGS. 9C and 9D illustrate the movement of the tip racks 16 with the top compartment 12 raised in order to agitate the pipette tips to assist in the drying process.

A method for washing pipette tips using the pipette tip washing device 10 will be described with reference to FIGS. 1-9D. One or more tip racks 16 containing pipette tips are loaded into the pipette washing device 10, although the present method may be utilized for other laboratory consumables. The one or more tip racks 16 are supported in the pipette tip washing device 10 by tip rack support 18. The one or more tip racks 16 may hold 24, 48, 96, 98, 100, 140, 168, 384, or 1536 pipette tips, by way of example, although the one or more tip racks 16 may hold other numbers of pipette tips. The pipette tip washing device 10 may be utilized with pipette tips with volumes of 10 μL-5 mL, such as 10 μL, 50 μL, 1 mL, or 5 mL pipettes, by way of example, with corresponding lengths between 30 mm-120 mm, although the pipette tip washing device 10 may be utilized with pipette tips with other sizes and configurations. Pipette tip washing device 10 may be utilized to clean both conductive and non-conductive pipette tips. Manifold body portions 48 having different numbers of liquid outputs 66 may be interchanged based on the number of pipette tips in the one or more tip racks 16.

One or more liquid washing or rinsing solutions are directed into the pipette tip washing device 10 through input ports 42. The liquid solutions may be pumped into the pipette tip washing device 10 by the pump in the external control source (not shown). In one embodiment, the liquid may be provided in a pressurized flow to assist in the cleaning process. The liquid solutions may be deionized water, bleach, hydrogen peroxide, one or more enzyme solutions, ethanol, detergent, purified water, water, ammonia, isopropanol, alcohol, a solution capable of substantially rinsing or decontaminating plastic, or combinations thereof, although other liquid solutions in other combinations may be utilized. In one example, the following liquid solutions are applied for washing/rinsing prior to draining: a) deionized water, b) deionized water and 5-10% bleach solution, c) deionized water, d) ethanol, although other liquid solutions may be applied in other combinations.

The liquid solutions enter the manifold dispensers 14 through the liquid input 58 in the manifold adapter 46. The liquid solutions are then directed through the manifold body portion 48. The liquid solutions exit the manifold body portion 48 at liquid outputs 66 and enter the middle compartment 20 to contact the pipette tips held in the one or more tip racks 16. The liquid outputs 66 may direct the liquid solution through the pipette tips or may possibly direct the pipette tips to uptake washing fluid for washing/rinsing.

The liquid solutions enter the middle compartment 20. Quartz floor 76 prevents the liquid solution from entering the bottom compartment 24. The liquid solution may exit the pipette washing device 10 through drain 78. In one example, the pipette tips may be submerged in the liquid solutions that are filled on top of the quartz floor 76 prior to being removed from the middle compartment 20 through drain 78.

The liquid solutions are then removed from the pipette washing device 10 through drain 78. In one example, 4 cycles of liquid solutions (water rinse, soap rinse, etc.) are directed into the middle compartment 20 prior to draining the fluids. After draining the liquid solutions, the pipette tips are at least substantially dried, although the pipette tips may be completely dried. In one example, the pipette tips are substantially dried by agitating the pipette tips, although other drying mechanisms may be utilized to substantially dry the pipette tips.

Throughout the wash process, the UV light source 26, by way of example, is engaged to expose the outer surfaces of the pipettes to ultraviolet light to sterilize the pipettes. The UV light source 26 directs light to the pipettes through the quartz floor 76, although UV light may be directed from other directions from other UV light sources, such as light sources 126 as illustrated in FIGS. 8A and 8B. The UV light source 26 may further direct light through the fiber optic needles 68 located in the openings of the liquid outputs 66 in the manifold body portion 48. The fiber optic needles 66 direct UV light to the inside of the pipette tips to provide sterilization of the interior surfaces of the pipette tips. Additionally, the pipette tips may be exposed to sound in an ultrasonic range from the one or more transducers 27, which direct the sound in the ultrasonic range into the washing chamber.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

That which is claimed:

1. A washing device comprising:
    a top compartment comprising a manifold dispenser, wherein the manifold dispenser comprises at least one liquid input and a plurality of liquid outputs that operably direct fluid to contact a plurality of laboratory consumables held by a rack, a number of liquid outputs being equal to a number of laboratory consumables such that each one of the fluid outputs operably directs fluid at a corresponding one of the laboratory consumables;
    a middle compartment positioned below the top compartment and comprising a washing chamber capable of receiving fluid output by the plurality of liquid outputs of the manifold dispenser, the washing chamber having a floor comprising a material transparent to ultraviolet (UV) light; and
    a bottom compartment positioned below the washing chamber, the bottom compartment having a light source mounted thereto, wherein the light source is capable of outputting UV light in the direction of the washing chamber and through the floor of the washing chamber.

2. The device of claim 1, wherein the rack comprises a tip rack and the plurality of laboratory consumables comprise a plurality of pipette tips.

3. The device of claim 2, wherein the tip rack is configured to hold 24, 48, 96, 384, or 1536 pipette tips.

4. The device of claim 1, wherein the washing chamber is capable of retaining liquid output by the plurality of liquid outputs such that the liquid cannot enter the bottom compartment.

5. The device of claim 1, wherein the washing chamber further comprises a waste drain operable to dispense retained liquid from the wash chamber.

6. The device of claim 1, wherein the top compartment comprises a plurality of manifold dispensers, each manifold dispenser comprising at least one liquid input and a plurality of liquid outputs that operably direct fluid to contact a plurality of laboratory consumables held by a respective rack, a number of liquid outputs of each manifold dispenser being equal to a number of laboratory consumables held by a respective rack such that each one of the fluid outputs operably directs fluid at a corresponding one of the laboratory consumables.

7. The device of claim 1, wherein the material transparent to UV light comprises quartz glass.

8. The device of claim 1, further comprising a plurality of fiber optic channels extending through the manifold dispenser at each of the plurality of liquid outputs.

9. The device of claim 8, wherein the light source is further coupled to the plurality of fiber optic channels.

10. The device of claim 8, wherein the plurality of liquid outputs each comprise a nozzle having an opening into which one of the plurality of fiber optic channels extends.

11. The device of claim 1, wherein the wash compartment is further configured to removably receive a wash sleeve, the wash sleeve comprising a material capable of reflecting at least a portion of the UV light output by the light source.

12. The device of claim 1, wherein the washing chamber has a plurality of walls and one or more of the plurality of walls comprise a material transparent to ultraviolet (UV) light.

13. The device of claim 12, wherein the middle compartment includes one or more additional light sources mounted thereto and proximate to one or more of the plurality of walls of the washing chamber, wherein the one or more additional light sources are capable of outputting UV light in the direction of the washing chamber and through one or more of the plurality of walls of the washing chamber.

14. The device of claim 1, further comprising one or more transducers capable of outputting sound in an ultrasonic range into the washing chamber.

15. The device of claim 1, further comprising one or more mechanical cylinders that operably agitate the rack.

16. The device of claim 1, wherein the middle compartment comprises a drawer capable of opening and closing.

17. The device of claim 1, wherein the manifold dispenser is capable of being raised and lowered vertically relative to the middle compartment.

\* \* \* \* \*